United States Patent
Gollier et al.

(10) Patent No.: US 7,532,779 B2
(45) Date of Patent: May 12, 2009

(54) SINGLE MODE (SM) FIBER OPTICAL READER SYSTEM AND METHOD FOR INTERROGATING RESONANT WAVEGUIDE-GRATING SENSOR(S)

(75) Inventors: Jacques Gollier, Painted Post, NY (US); Garrett A. Piech, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/002,458

(22) Filed: Dec. 17, 2007

(65) Prior Publication Data

US 2008/0101745 A1    May 1, 2008

Related U.S. Application Data

(62) Division of application No. 11/058,155, filed on Feb. 14, 2005, now Pat. No. 7,346,233.

(51) Int. Cl.
*G02B 6/00* (2006.01)
*C12M 1/34* (2006.01)

(52) U.S. Cl. .............. 385/12; 385/27; 385/33; 385/37; 385/39; 435/287.1

(58) Field of Classification Search ........... 385/12, 385/27, 33, 37, 39; 435/287.1
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,396,325 A | 3/1995 | Carome et al. | 356/128 |
| 6,014,204 A | 1/2000 | Prahl et al. | 356/73 |
| 7,167,615 B1 | 1/2007 | Wawro et al. | 385/37 |
| 2002/0009812 A1 | 1/2002 | Miura et al. | 436/518 |
| 2002/0127565 A1 | 9/2002 | Cunningham et al. | 435/6 |
| 2002/0168295 A1 | 11/2002 | Cunningham et al. | 422/82.05 |
| 2003/0004412 A1* | 1/2003 | Izatt et al. | 600/425 |
| 2003/0017580 A1 | 1/2003 | Cunningham et al. | 435/287.2 |

(Continued)

FOREIGN PATENT DOCUMENTS

DE    43 05 830    8/1994

(Continued)

OTHER PUBLICATIONS

M. Wiki et al., "Novel integrated optical sensor based on a grating coupler triplet", Biosensors & Bioelectronics, vol. 13, 1998, pp. 1181-1185.

(Continued)

*Primary Examiner*—Frank G Font
*Assistant Examiner*—Michael P Mooney
(74) *Attorney, Agent, or Firm*—William J. Tucker; Thomas R. Beall

(57) ABSTRACT

An optical reader system is described herein which has a single mode (SM) optical fiber launch/receive system that uses one or more SM optical fibers to interrogate a biosensor and does not use multimode (MM) optical fibers to interrogate the biosensor. The use of the SM optical fiber launch/receive system effectively reduces angular sensitivity, reduces unwanted system reflections, improves overall angular tolerance, and improves resonant peak reflectivity and resonant peak width. Two specific embodiments of the SM optical fiber launch/receive system are described herein which include: (1) a dual fiber collimator launch/receive system; and (2) a single fiber launch/receive system that interrogates the biosensor at a normal incidence.

12 Claims, 16 Drawing Sheets

U.S. PATENT DOCUMENTS

| | | | |
|---|---|---|---|
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2004/0132172 A1 | 7/2004 | Cunningham et al. | 435/287.2 |
| 2004/0132214 A1 | 7/2004 | Lin et al. | 436/518 |
| 2004/0145752 A1 | 7/2004 | Angeley | 356/521 |
| 2004/0151626 A1 | 8/2004 | Cunningham et al. | 422/58 |
| 2004/0223881 A1 | 11/2004 | Cunningham et al. | 422/82.05 |
| 2005/0070027 A1 | 3/2005 | Gollier et al. | 436/518 |

FOREIGN PATENT DOCUMENTS

| | | |
|---|---|---|
| EP | 1 239 279 | 9/2002 |
| WO | 94/25850 | 11/1994 |

OTHER PUBLICATIONS

M. Wiki et al., "Wavelength-interrogated optical sensor for biochemical applications", Optics Letters, Apr. 1, 2000, vol. 25, No. 7, pp. 463-465.

K. Cottier et al., "Label-free highly sensitive detection of (small) molecules by wavelength interrogation of integrated optical chips", Sensors and Actuators B, vol. 91, 2003, pp. 241-251.

F. Lemarchand et al., "Study of the resonant behaviour of waveguide gratings: increasing the angular tolerance of guided-mode filters", J. Opt. A: Pure Appl. Opt. 1, 1999, pp. 545-551.

D.K. Jacob et al., "Normally incident resonant grating reflection filters for efficient narrow-band spectral filtering of finite beams", J. Opt. Soc. Am. A, vol. 18, No. 9, Sep. 2001, pp. 2109-2120.

F. Lemarchand et al., "Increasing the angular tolerance of resonant grating filters with doubly periodic structures", Optics Letters, Aug. 1, 1998, vol. 23, No. 15, pp. 1149-1151.

\* cited by examiner

* X axis is wavelength (nm)
  Y axis is resonant intensity (counts)

US 7,532,779 B2

SINGLE MODE (SM) FIBER OPTICAL READER SYSTEM AND METHOD FOR INTERROGATING RESONANT WAVEGUIDE-GRATING SENSOR(S)

CROSS REFERENCE TO RELATED APPLICATION

This application is a divisional application of U.S. patent application Ser. No. 11/058,155, filed Feb. 14, 2005 now U.S. Pat. No. 7,346,233.

BACKGROUND OF THE INVENTION

1. Field of the Invention

The present invention relates to a single mode (SM) fiber optical reader system and method for interrogating a resonant waveguide grating (RWG) sensor to monitor biological events on top of the RWG sensor without suffering from problems caused by parasitic reflections, while preserving wide angular tolerance and minimizing sensitivity to angular changes.

2. Description of Related Art

Manufacturers of optical reader systems are always trying to design a new and improved optical reader system that can be used to interrogate a biosensor (e.g., RWG sensor, surface plasmon resonance (SPR) biosensor) to determine if a biomolecular binding event (e.g., biological binding of ligands with analytes) occurred on a top surface of the biosensor. One such new and improved optical reader system is the subject of the present invention.

BRIEF DESCRIPTION OF THE INVENTION

The present invention includes an optical reader system which has a single mode (SM) optical fiber launch/receive system that uses one or more SM optical fibers to interrogate a biosensor and does not use multimode (MM) optical fibers to interrogate the biosensor. The use of the SM optical fiber launch/receive system effectively reduces angular sensitivity, reduces unwanted system reflections, and improves resonant peak reflectivity and resonant peak width. Two specific embodiments of the SM optical fiber launch/receive system are described herein which include: (1) a dual fiber collimator launch/receive system; and (2) a single fiber launch/receive system that interrogates the biosensor at a normal incidence.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
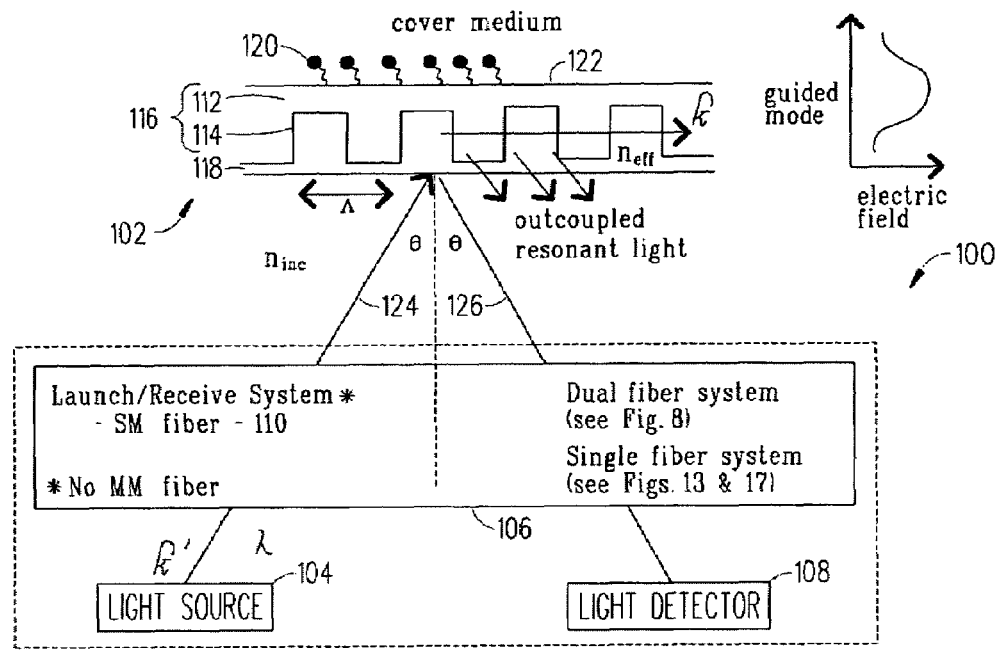
FIG. 1 is a diagram showing an optical reader system which has a SM optical fiber launch/receive system in accordance with the present invention.

Referring to FIG. 1, there is a diagram that illustrates an optical reader system 100 (interrogation system 100) which can interrogate one or more RWG sensors 102 (one shown) to monitor biological events on top of the RWG sensor 102. The optical reader system 100 includes a light source 104 (e.g., SLD, laser), a launch/receive system 106 and a light detector 108 (e.g., photodiode, spectrograph, CCD camera). In accordance with the present invention, the launch/receive system 106 utilizes SM optical fiber 110 (plus other optics) to interrogate the RWG sensor 102 and does not use any multimode (MM) optical fiber(s) to interrogate the RWG sensor 102. The advantages of using only SM optical fiber 110 within the launch/receive system 106 and two exemplary embodiments of the SM optical fiber launch/receive system 106 are described in detail after a brief description is provided about the structure and functionality of the RWG sensor 102.

As shown in FIG. 1, the RWG biosensor 102 includes a thin (~100 nm) layer of material 112 which is deposited on the surface of a diffraction grating 114, forming a waveguide 116. The diffraction grating 114 is typically formed in a substrate material 118 by embossing, holography, or other methods. Alternatively, the diffraction grating 114 can be formed in the material 112 itself. Molecules 120 or bulk fluids (cover medium) may be deposited on a top surface 122 of the RWG sensor 102 which alter the index of refraction at the top surface 122 of the RWG sensor 102. By probing the diffraction grating 114 with an optical beam 124, one can detect this change (~1 part per million) in the refractive index on the top surface 122 of the sensor 102. The top surface 122 of the RWG sensor 102 may also be coated with biochemical compounds (not shown) that only allow surface attachment of specific complementary molecules 120, enabling the RWG sensor 102 to be both highly sensitive and highly specific. Such RWG sensors 102 can be interrogated to detect a wide variety of chemical compounds or biomolecular binding events (e.g., binding of a drug to a protein) on the top surface 122. An array of RWG sensors 102 may be used in a microplate (for example) that enables high throughput drug or chemical screening systems. For a more detailed discussion about the structure and functionality of the RWG biosensor 102 reference is made to the following document:

U.S. Pat. No. 4,815,843 entitled "Optical Sensor for Selective Detection of Substances and/or for the Detection of Refractive Index Changes in Gaseous, Liquid, Solid and Porous Samples".

The contents of this document are incorporated by reference herein.

Figure 2:
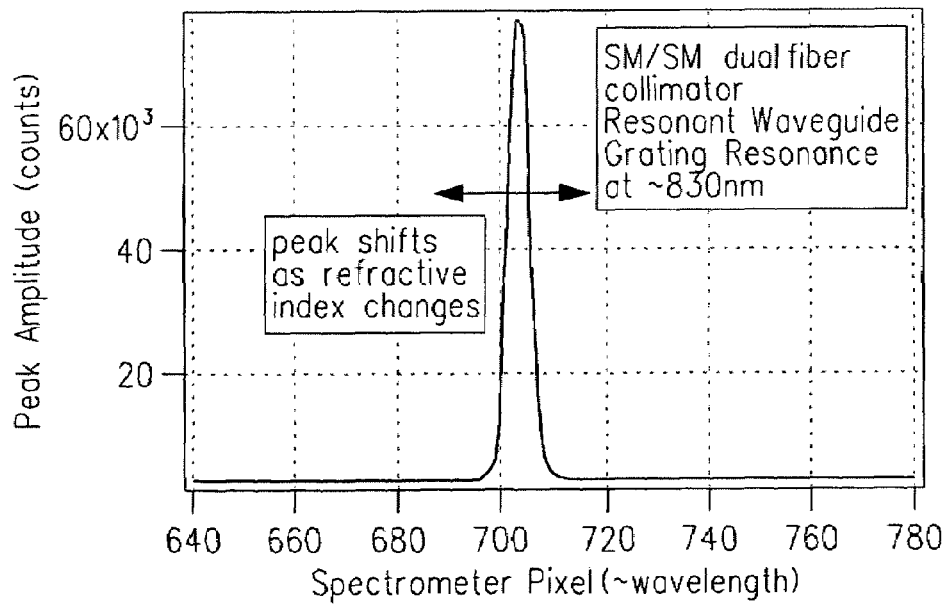
FIG. 2 is a graph indicating an optical resonance from a RWG sensor.

One method that can be used to interrogate the RWG sensor 102 in order to detect a biomolecular binding event is known as spectral interrogation. Spectral interrogation entails illuminating the RWG sensor 102 with a multi-wavelength or broadband beam of light 124, collecting the reflected light 126, and analyzing the spectrum of the reflected light 126 with a spectral dispersing device such as a spectrometer 108. An example of a reflection spectrum from such a RWG sensor 102 is shown in FIG. 2. When biomolecular binding occurs at the surface 122 of the RWG sensor 102, the resonance shifts slightly in wavelength, and it is this shift in the resonance wavelength that is detected at the spectrometer 108. A second configuration that also uses spectral interrogation for interrogating the RWG sensor 102 entails using a tunable optical element such as laser (or Fabry-Perot filter, . . . ) as the source to modulate the wavelength of the input beam and then the power reflected by the sensor is measured by a simple detector (e.g. photodiode, . . . ) to detect the resonance shifts.

It is well known that the use of fiber optics 110 is an efficient way of interrogating arrays of RWG sensors 102, because optical fiber 110 can be used to easily route, split, and collect optical beams 124 and 126 from arrays of RWG sensors 102. However, there are a number of important aspects that need to be considered in order to create a robust and sensitive optical interrogation system 100 which utilizes optical fiber 110. These aspects are described in detail below and include: (1) quality of spectrum; (2) angular sensitivity; and (3) angular tolerance.

Quality of Spectrum

For the spectral interrogation method, the quality of the spectrum in the reflected light 126 is critically important. Ideally, the reflected spectrum should contain only resonant reflected radiation, and should be free from Fresnel reflections that are caused by sensor interfaces, and other "parasitic" reflections within the optical path. These extraneous reflections distort the resonant peak shape, making it more difficult to accurately locate the resonant peak. These extraneous reflections can also make the optical system respond to resonant peak shifts in a non-linear manner. And, if these extraneous reflections change in time, they can cause extra noise or even false resonant peak shifts that behave like a binding event. To combat these problems, some have designed RWG sensors with multiple input and output gratings. These types of RWG sensors are described in the following documents:

M. Wiki, R. E. Kunz, G. Voirin, K. Tiefenthaler, and A. Bernard, "Novel integrated optical sensor based on a grating coupler triplet," Biosensors and Bioelectronics 13 (1998) 1181-1185.

M. Wiki and R. E. Kunz, "Wavelength-interrogated optical sensor for biochemical applications," Optics Letters 25, No. 7, 463-465 (2000).

K. Cottier, M. Wiki, G. Voirin, H. Gao, and R. E. Kunz, "Label-free highly sensitive detection of (small) molecules by wavelength interrogation of integrated optical chips," Sensors and Actuators B 91 (2003) 241-251.

The contents of these documents are incorporated by reference herein.

However, the designs of these types of RWG sensors are very complicated, and make the fabrication of the sensor itself more difficult. The present invention can address this problem by using a SM optical fiber launch/receive system 106 which can create a high quality resonance spectrum without needing a complicated design of a RWG sensor 102.

Angular Sensitivity

An additional concern for the spectral interrogation method is the dependence of the resonant signal wavelength on the incident angle θ. If the incident angle θ changes, then the resonant wavelength will shift. This can be seen from the approximate RWG resonant condition:

$$\sin\theta = \Lambda n_{\mathit{eff}} - \frac{\lambda}{\Lambda}. \quad \text{(equation 1)}$$

Here Λ is the pitch of the grating 114, θ is the angle of the incident optical beam 124, $n_{\mathit{eff}}$ is the effective index of the waveguide 116, and λ is the wavelength of the resonance. One can then calculate, $$\frac{d\lambda}{d\theta} \approx -\Lambda, \quad \text{(equation 2)}$$

when the following approximation is made cos θ~1 (small incident angle). For a grating pitch Λ of 500 nm this evaluates to 8.7 nm/deg or 500 pm/mrad. This means that, if the global instrument accuracy target is, for example, in the range of 0.1 pm, then angular misalignments need to be kept below two tenths of a microradian. Thus, in the absence of other filtering effects, such an interrogation system is highly sensitive to the overall angular positioning of the RWG sensor 102. This sensitivity to angular positioning is particularly problematic if a microplate incorporating an array of RWG sensors 102 must be removed from the reading optics and reinserted during the course of an assay. A second reason to decrease the angular sensitivity is that when one uses the invention one frequently makes relative measurements by making a comparison between a "sample" signal and a "reference" signal. In absence of any filtering, this means that the angular stability between the 'reference' optical path and the 'sample' optical path should remain stay stable within less than two tenths of a microradian. How the use of exclusively SM optical fiber 110 within the launch/receive system 106 reduces this angular sensitivity by orders of magnitude is described below.

Angular Tolerance

Figure 3:
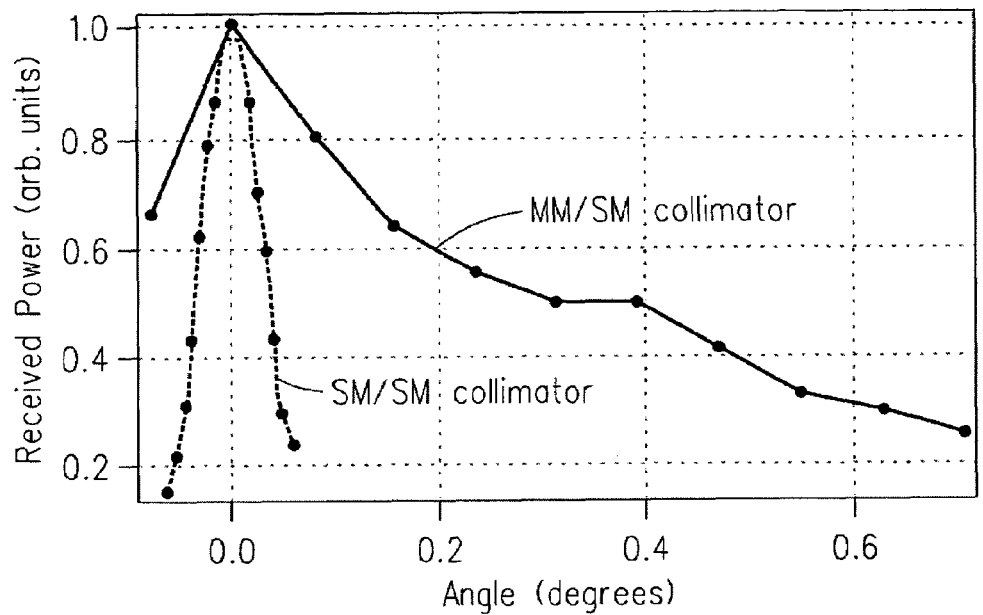
FIG. 3 is a graph of power received vs. incident angle for a SM launch/SM receive fiber system and for a MM launch/SM receive fiber system.

FIG. 3 shows an example of the angular tolerance of a multimode (100 µm core) launch fiber/single mode (5.5 µm core) receive fiber and a single mode (5.5 µm core) launch fiber/single mode (5.5 µm core) receive fiber. Here one can clearly observe the wider angular acceptance angle of the multimode fiber system. Since RWG sensors 102 may not be perfectly flat, or may be placed on the interrogation optics to within a range of angles, one desires a fiber system with a wide collection angle tolerance. This leaves a designer with two options in order to create wide angular tolerances use large core (multimode) fiber, or use short focal length lenses which necessitates interrogation of the sensor with small beam diameters.

As mentioned above, the use of SM fiber 110 is important for overall spectrum quality and stability of the optical signal. Due to the small core diameter of SM fiber 110, this forces the use of a short focal length lens to keep the angular tolerance as high as possible in order to remain compatible with microplates having significant angular deformation. However, the use of the short focal length lens produces a small beam at the RWG sensor 102 which in turn causes an undesirable reduction in reflection efficiency and an undesirable increase in resonant spectral width. While one cannot eliminate these detrimental effects when using smaller beam sizes, the SM optical fiber launch/receive system 106 described below can, with the judicious use of a normally incident SM optical fiber lens, improve the overall angular tolerance of the interrogation system 100, while minimizing the price paid in reflection efficiency and resonance spectral width.

SM Optical Fiber Launch/Receive System 106

Figure 4:
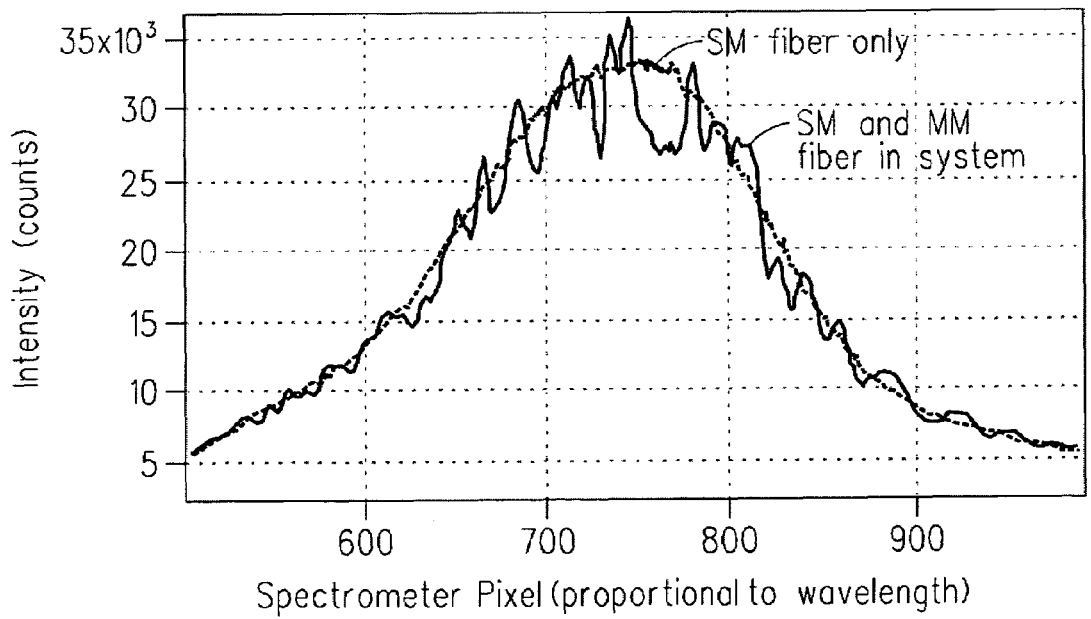
FIG. 4 is a graph of the spectrum of a superluminescent diode (SLD) reflection off a mirror observed with a entirely SM fiber path, and a spectrum observed when using a MM collection fiber.
Figure 5:
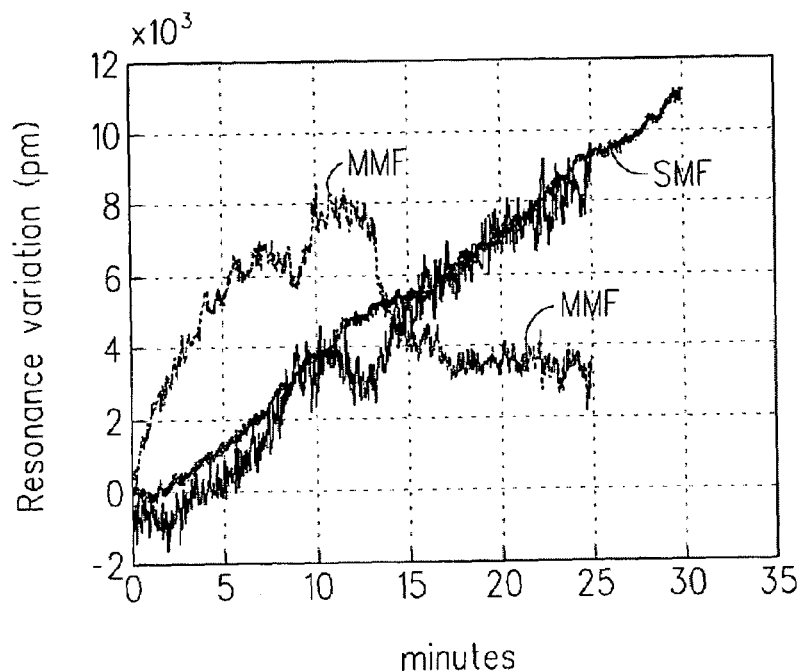
FIG. 5 is a graph illustrating a resonance wavelength as a function of time for a SM launch/SM receive fiber system compared with a MM launch/SM receive fiber system.

A primary advantage of using only SM optical fiber 110 within the launch/receive system 106 is the elimination of multiple spatial modes in the fiber path. FIG. 4 shows the spectrum of a broadband superluminescent diode (SLD) optical light source 104 that was obtained when exclusively SM fiber, and SM fiber mixed with MM fiber was present in the optical path. The high frequency structure present on the spectrum obtained with mixed SM/MM fiber is due to multipath (multiple spatial mode) interference effects. This high frequency structure on the spectrum can distort the shape of an optical resonance from the RWG sensor 102 and prevent accurate estimation of its wavelength. Shaking or otherwise mode-scrambling the multimode sections of the MM optical fiber can mitigate these effects, but not necessarily eliminate them. However, if all of the optical fiber in the launch/receive system 106 is SM optical fiber 110 then these multimode effects can be eliminated for the system's band of operating wavelengths. A comparison of measurements of the resonance wavelength as a function of time, when observed with a SM/SM optical fiber launch/receive system 106 and a MM/SM optical fiber launch/receive system is shown in FIG. 5. It can be seen that the resonance wavelength is more stable for the exclusive SM optical fiber launch/receive system 106.

As described above, the range of collection angles that a lens, in conjunction with a small core diameter (e.g. single mode) fiber, collects is greatly reduced compared to a lens with a large core (e.g. multimode) fiber. While at first glance this reduced angular tolerance seems to make the SM optical fiber launch/receive system 106 less desirable, upon further inspection this reduced range of angles can be seen to be a distinct advantage for practical systems. As has also been described above, the RWG sensor 102 will change resonant wavelength when tilted with respect to the input optical beam 124. However, when SM optical fiber 110 is used on the receive end of the lens (collimator) this means that only a select angular band will be passed which in turn reduces the effects of these shifts in resonant wavelength.

Figure 6:
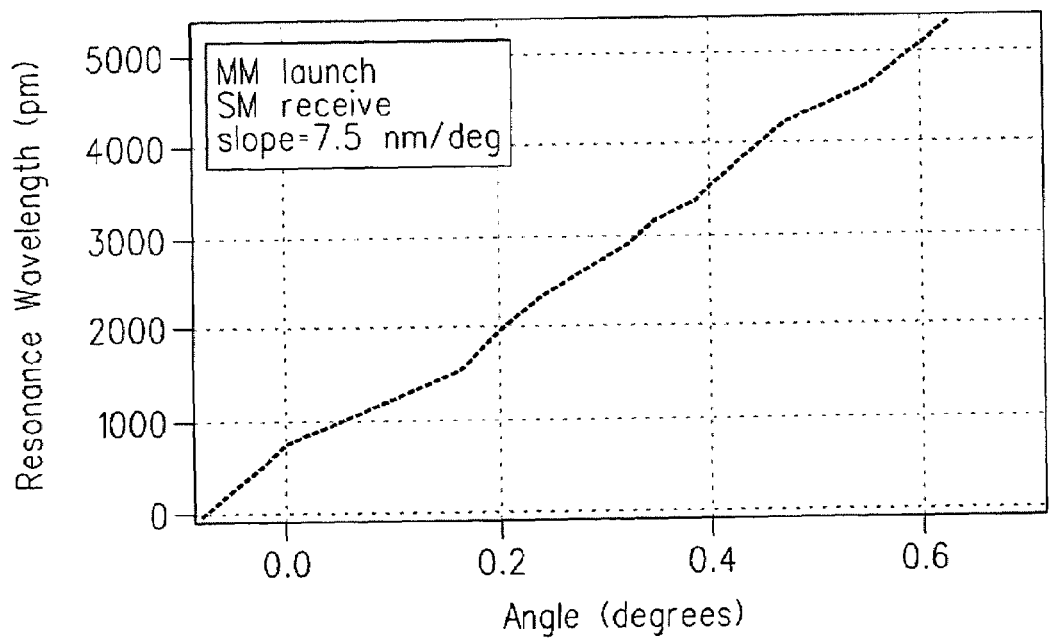
FIG. 6 is a graph illustrating a resonant wavelength vs. angle of incidence for a MM launch/SM receive fiber system.
Figure 7:
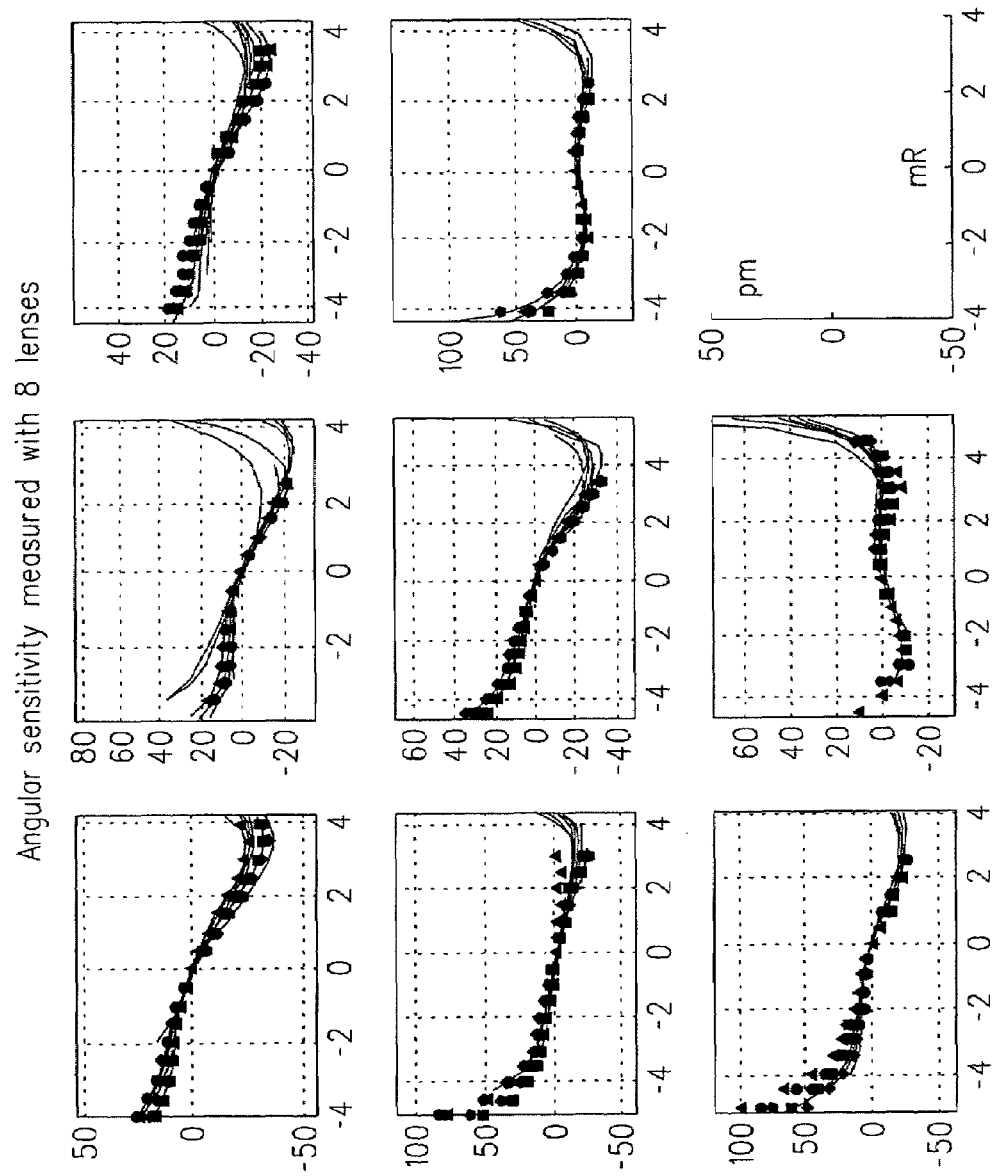
FIG. 7 are graphs illustrating a resonant wavelength vs. angle of incidence for SM launch/SM receive fiber system measured with 8 different collimators close to normal incidence.

Thus, when SM optical fiber 110 is used with the lens (collimator) this effectively creates a fiber/lens system that behaves as an "angular filter" which can emit or receive rays of light 124 and 126 that are from a very narrow cone of angles. The approximate cone angle is given by $\Delta\theta = d/f$, (d=core diameter, f=focal length of lens) so that for example when Corning FlexCor780 (5 µm core SM fiber) and an f=2 mm lens are used then $\Delta\theta \sim 2.5$ mrad. A comparison of the angular sensitivity of a SM launch/SM receive system 106 and a MM launch/SM receive system is made in FIGS. 6 and 7. The MM launch/SM receive system has a $d\lambda/d\theta = 7.5$ nm/deg, which is close to the 8.7 nm/deg mentioned above. Indeed, this observed value of 7.5 nm/deg (430 pm/mrad) can be more accurately predicted if dispersion effects of the waveguide are taken into account. However, for the SM launch/SM receive system 106, one observes a wavelength sensitivity of only ~0.18 nm/deg (10 pm/mrad). This SM angular sensitivity is almost two orders of magnitude less than the MM launch/SM receive system.

When modeling identical SM optical fiber 110 at the light emission and light detection, it may be shown that the resonance wavelength is, in principle, insensitive to any angular misalignment of the RWG sensor 102 because of this filtering effect. Indeed, it is only optical defects and aberrations that can create any residual wavelength change with angle. As such, to achieve angular sensitivities that are as low as possible, one should make the SM optical fiber launch/receive system 106 in a manner which takes into account the following parameters:

Optical quality: the aberration generated by the lens or by the sensor surface deformation should be as low as possible.

Cleanliness: the optics and the sensor should be free of any particle/dust.

It is important that the emission fiber and the detection fiber are perfectly identical.

Any light propagating into the cladding of the SM optical fiber 110 should be removed.

In other words, any system effects that create a less than "ideal" optical path will create residual angular sensitivities for the interrogation system 100. Even so, the practical angular sensitivity of the interrogation system 100 can easily be <10 pm/mRd. Such a low wavelength shift with angle can make the removal/reinsertion of the RWG sensor(s) 102 during a biochemical test feasible, since small angular errors will not significantly perturb the resulting signal.

Dual Fiber Launch/Receive System

First Embodiment

Figure 8:
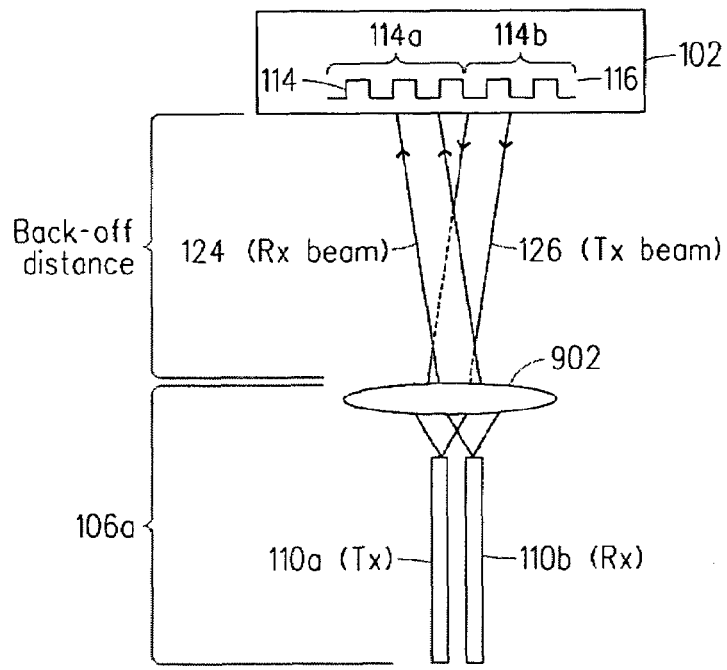
FIG. 8 is a block diagram illustrating the basic components of a dual fiber collimator launch/receive system that is interrogating a RWG sensor in accordance with one embodiment of the present invention.

Referring to FIG. 8, there is shown a dual fiber collimator launch/receive system 106a in accordance with one embodiment of the present invention. As described below, the dual fiber collimator launch/receive system 106a which is constructed with two SM optical fibers 110a and 110b is an extremely advantageous tool for interrogating a RWG sensor 102. By controlling the separation distance or "back-off distance" of the collimator 902 from the biosensor 102, one effectively creates a separate input grating 114a and an output grating 114b.

The separation of these input and output gratings 114a and 114b increases as the collimator "back-off" distance is increased. The use of separate input and output gratings 114a and 114b allows one to reject Fresnel reflections and "parasitic" reflections caused by multiple reflections from various material interfaces in the RWG sensor 102. Fortunately, the reduction in Fresnel and parasitic reflection intensity is much greater than the reduction in resonance reflection intensity, because the resonance mode propagates through the waveguide 116 before being coupled out. This guided mode decay is typically characterized by the RWG sensor's leakage coefficient "alpha", or $\alpha$, where the intensity of the guided mode, I, as a function of position x is given by: $I \approx I_0 e^{-\alpha x}$.

Figure 9:
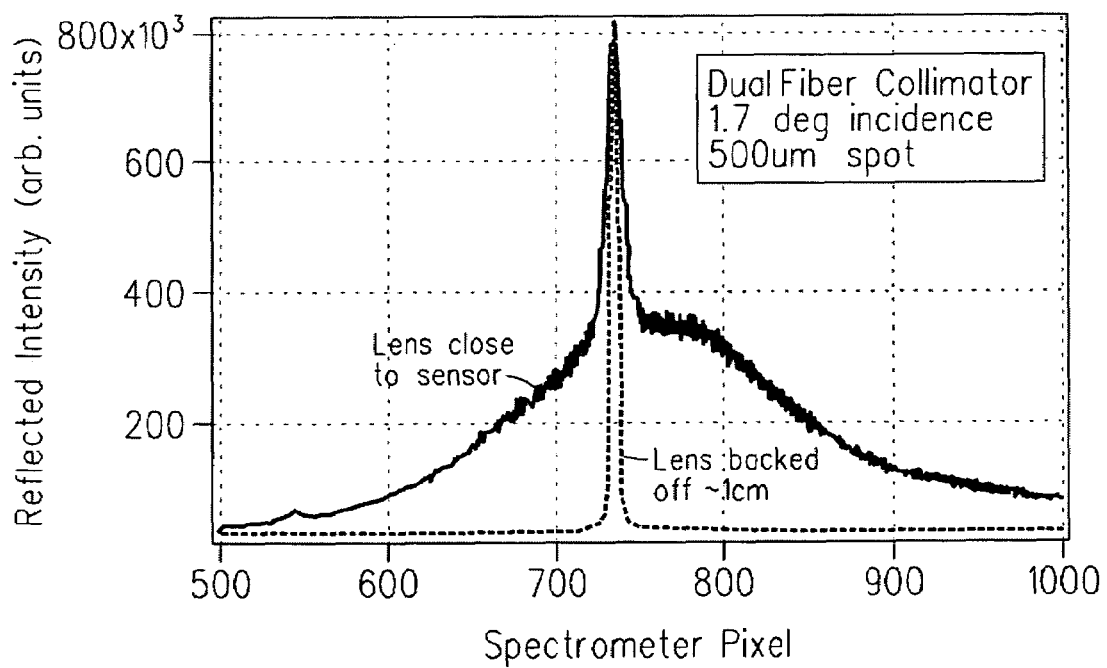
FIG. 9 is a graph illustrating a reflected spectrum from a RWG sensor using the dual fiber collimator launch/receive system with and without collimator "back-off"
Figure 10:
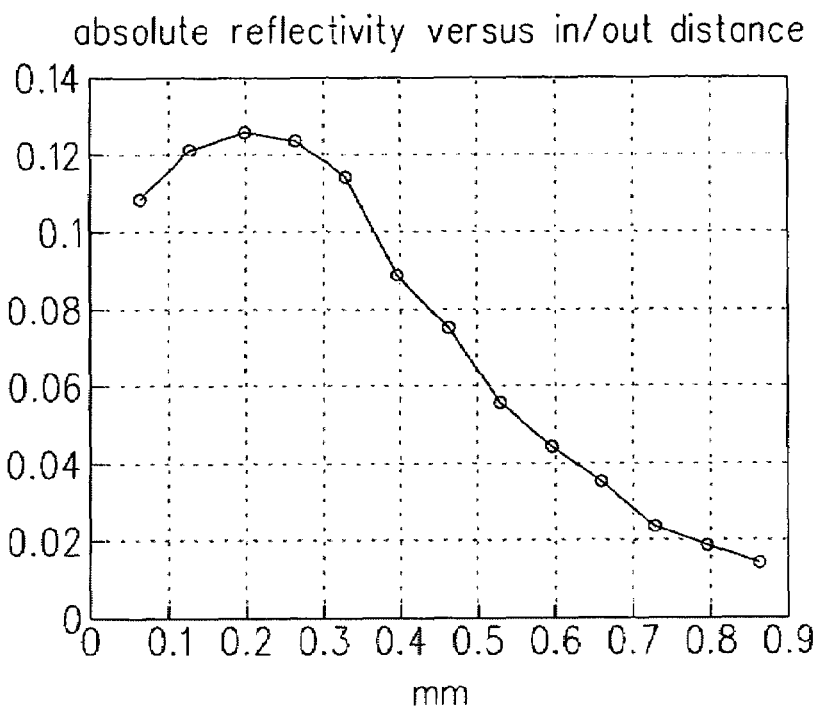
FIG. 10 is a graph illustrating a resonance intensity as a function of collimator back-off using the dual fiber collimator launch/receive system.
Figure 11:
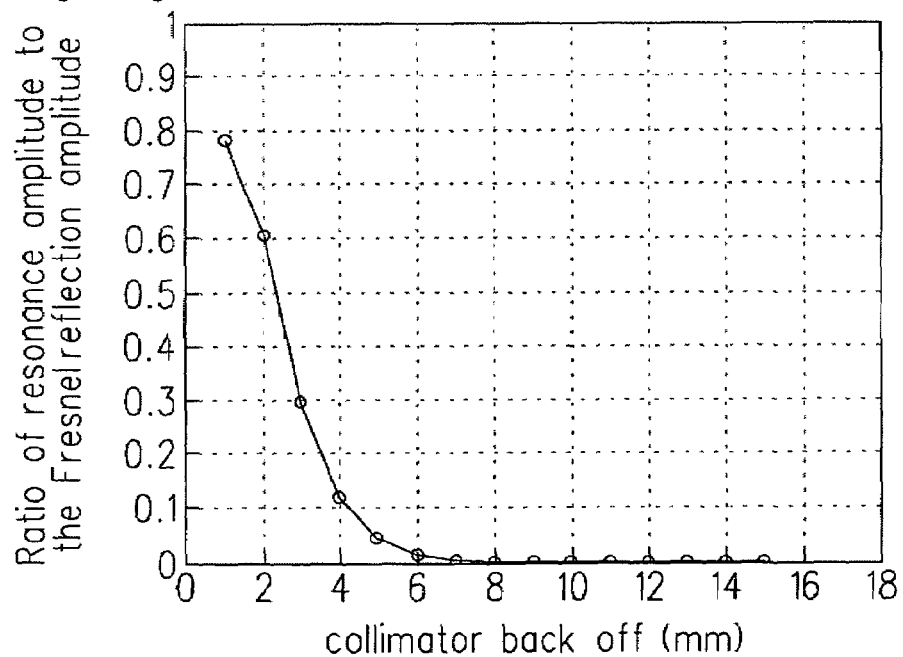
FIG. 11 is a graph illustrating a ratio of Fresnel reflection amplitude to the peak power as a function of collimator back-off using the dual fiber collimator launch/receive system.

Spectra obtained with and without collimator "back-off" are shown in FIG. 9. The progressive effect of the "back-off" distance upon the resonance and Fresnel reflection intensity are measurements displayed in FIGS. 10 and 11. The cost associated with backing off the fiber collimator 902 is a slow reduction in resonance signal amplitude. Thus, if the coupling loss coefficient, $\alpha$, is carefully considered, one can design the RWG sensor 102 for high resonance efficiency and very little Fresnel or parasitic reflection. In designing the RWG sensor 102 it should be noted that the value of $\alpha$ effects the optimum collimator standoff distance. For example, this means that for an RWG sensor 102 with a higher "alpha" one would operate the collimator 902 closer to the RWG sensor 102 than for a RWG sensor 102 with a lower "alpha".

If one measures the amplitude of the resonant peak reflection as a function of the "back-off" distance, then one may actually make a measurement of this grating loss parameter, $\alpha$. This is possible because of the fact that as the "back-off" distance increases the separation between the input and output areas of the grating 114a and 114b also increases. Then, as long as the input and output gratings 114a and 114b are completely separated, the returned resonant signal decays exponentially in relation with the input/output separation distance. Such a measurement is useful for designing RWG sensors 102 and for performing quality control of RWG sensor arrays.

Figure 12:
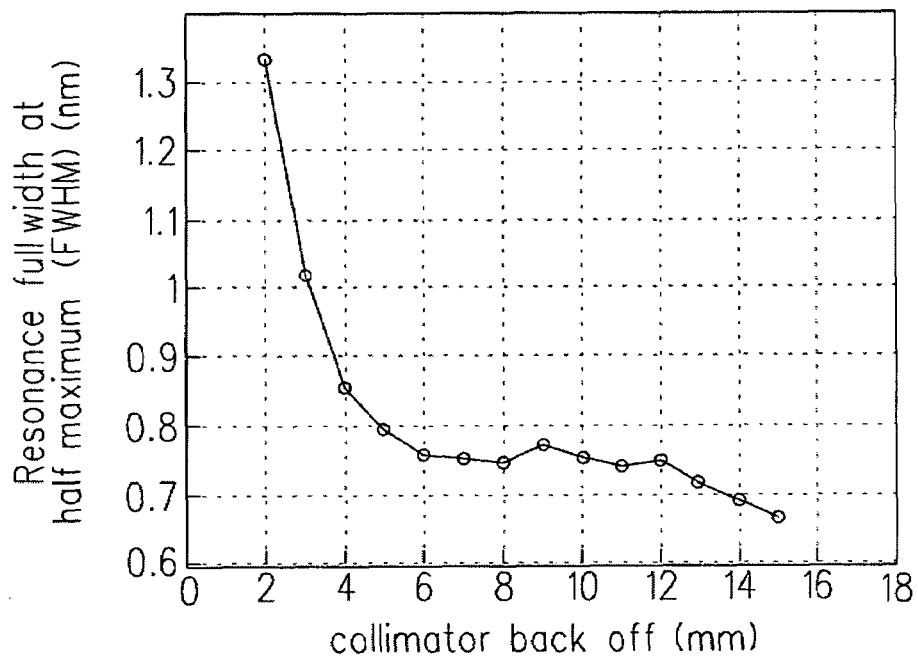
FIG. 12 is a graph illustrating a resonance full width at half maximum as a function of collimator back-off using the dual fiber collimator launch/receive system.

An additional benefit of using the dual fiber collimator launch/receive system 106a with "back-off" is that the resonance width decreases as the "back-off" distance is increased. This width decrease is the consequence of the fact that the beam is propagating over longer distance inside the RWG. This is in fact one of the advantages of using a continuous grating rather than the discrete gratings connected by a waveguide as described in the literature listed above. The narrower the resonance, the more accurately one can determine its position, for a fixed signal-to-noise ratio. An example of this resonance narrowing effect is shown in the measurements displayed in FIG. 12.

Single Fiber Launch/Receive System 106b

Second Embodiment

With the dual fiber collimator launch/receive system 106a outlined in the previous section, each SM fiber 110a and 110b is inherently off the optical axis of the lens 902, so that interrogation is performed at a non-normal incident angle. At such a non-normal incident angle, it may be shown that the peak reflectivity of the RWG sensor 102 rapidly decreases when decreasing the beam diameter and, simultaneously, the spectral width of the resonance also increases. Both of these effects negatively impact the performance of the interrogation system 100. Smaller spot size is detrimental to the performance because the interrogation system 100 interrogates a smaller region of the RWG sensor 102 and as such becomes more sensitive to local perturbations and non-uniformities. Increased resonant spectral width is also detrimental, because the ultimate resolution (in wavelength) of the interrogation system 100 increases with the resonance width and hence wider peaks lead to a degraded resolution.

Figure 13:
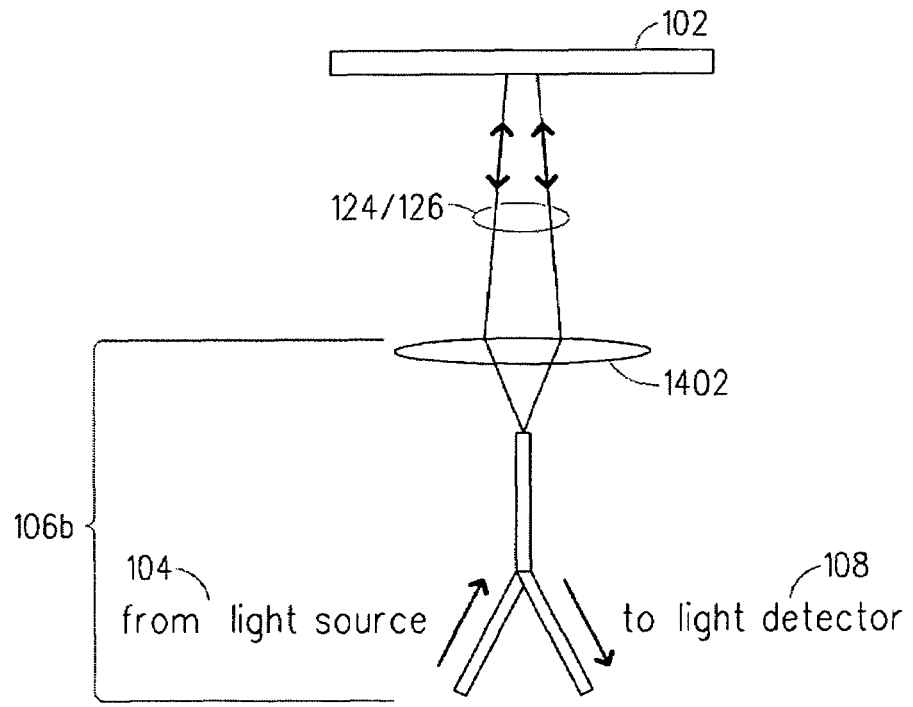
FIG. 13 is a diagram illustrating the basic components of a single fiber launch/receive system that is interrogating a RWG sensor at a normal incidence in accordance with another embodiment of the present invention.

On the other hand, a smaller spot size does have one significant practical advantage. Real instruments have to deal with the non-flatness of the microplates in which RWG sensors 102 are located. So, unless the interrogation system 100 realigns the lenses 1402 (only one shown in FIG. 13) for every new measurement, the angular tolerance of the interrogation system 100 has to be higher than the typical angular deformations of the micoplate/RWG sensors 102. The angular tolerance is directly dictated by the beam diameter over the diffraction grating 114, the smaller diameters give better angular tolerances. That is, from the limitations of diffraction, the angular acceptance of the interrogation system 100 is roughly dictated by the diffraction limit of the spot used to interrogate the RWG sensor 102 as follows:

$$\Delta\theta \approx \frac{\lambda}{d_{spot}} * 0.5 \qquad \text{(equation 3)}$$

where $\Delta\theta$ is the range of angles that may be collected, $\lambda$ is the wavelength of the incident illumination 124, and $d_{spot}$ is the diameter of the beam 124 at its focus on the RWG sensor 102. This all results in a dilemma: one would like to use large spot sizes to get a good resonance definition and spatial averaging, but one would also like to use small spot sizes to get a good angular tolerance.

Figure 14:
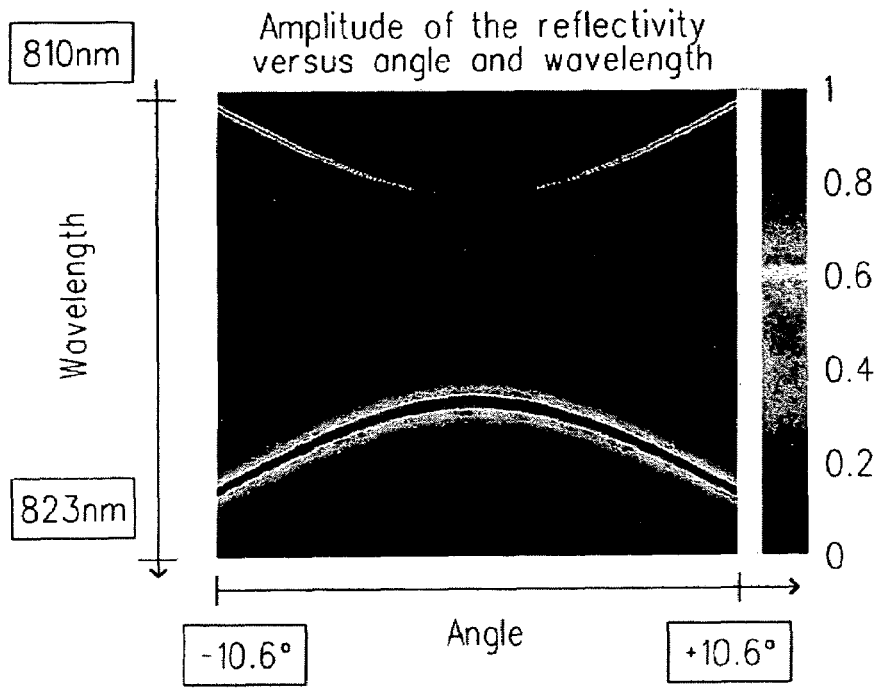
FIG. 14 is a 2D-plot illustrating the results of calculating the resonance intensity as a function of incident angle and wavelength for a RWG sensor.

The solution to this dilemma is to interrogate the RWG sensor 102 at a normal incidence. In this case, the single fiber launch/receive system 106b would use a single SM optical fiber 110 and one lens 1402 (see FIG. 13) aligned with one another such that when the optical beam 124 is reflected by the RWG sensor 102, the reflected beam 126 comes back on itself and into the SM optical fiber 110. In this case, the SM optical fiber 110 is used for both light injection and detection. The advantage of this configuration is that one can drastically decrease the diameter of the optical beam 124/126 over the RWG sensor 102 and keep excellent peak reflectivity coefficients as well as resonance width. This is because the wavelength dependence of the resonance near normal incidence is actually a parabolic function of angle, rather than the linear approximation depicted in equation no. 1, which is valid at larger angles. A plot of this parabolic function of resonant reflection efficiency as it relates to wavelength and angle for forward and reverse propagating modes in the RWG sensor 102 is shown in FIG. 14. In this plot, the upper parabola represents the intensity of the forward propagating mode. And, the lower parabola represents the intensity of the reverse propagating waveguide mode. For a more detailed discussion about this phenomenon, reference is made to the following documents:

- F. Lemarchand, A. Sentenac, and H. Giovannini, "Increasing the angular tolerance of resonant grating filters with doubly periodic structures," Opt. Lett. 23, No. 15, pp. 1149-1151 (1998).
- F. Lemarchand, A. Sentenac, E. Cambril, and H. Giovannini, "Study of the resonant behaviour of waveguide gratings: increasing the angular tolerance of guided-mode filters," J. Opt. A: Pure Appl. Opt. 1 (1999), pp. 545-551.
- D. Jacob, S. Dunn, and M. Moharam, "Normally incident resonant grating reflection filters for efficient narrow-band spectral filtering of finite beams," J. Opt. Soc. Am. A 18, No. 9, pp. 2109-2120 (2001).

The contents of these documents are incorporated by reference herein.

One can clearly see in FIG. 14 that near zero angle (normal incidence), the resonant wavelength changes only slowly with angle i.e $d\lambda/d\theta$ approaches zero. Using this information and equation no. 3, one may obtain the graphs in FIGS. 15-16 which show the peak width calculated as a function of the beam diameter. As can be seen, one can considerably decrease the beam diameter at normal incidence and still maintain resonance quality.

However, since there is no separation of the illumination and collection regions as in the dual fiber collimator launch/receive system 106a, interrogation at normal incidence with a single fiber launch/receive system 106b suffers from the drawback that Fresnel and other parasitic reflections will be collected along with the resonant reflections.

Figure 17:
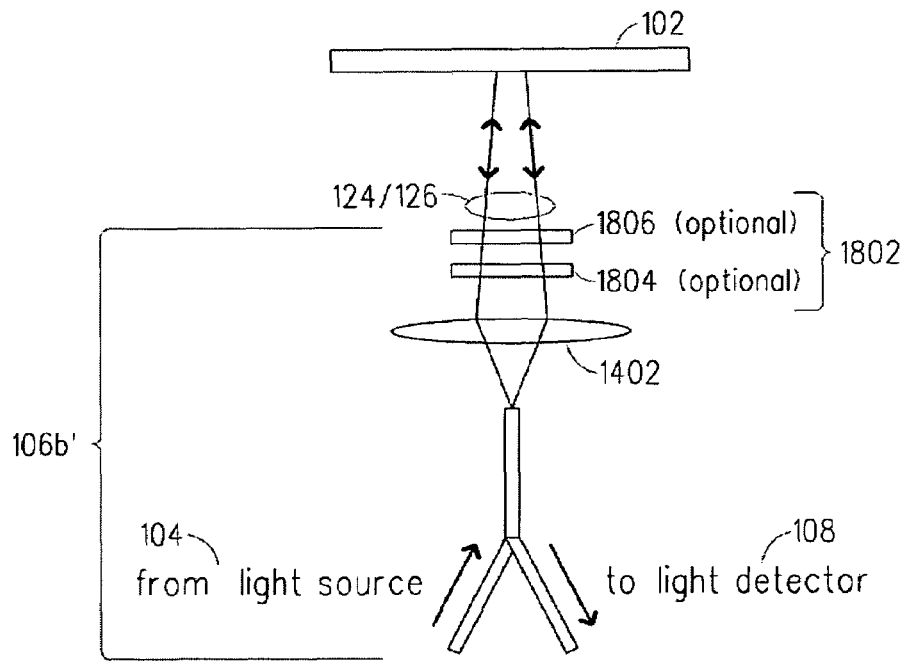
FIG. 17 is a block diagram illustrating the basic components of a single fiber collimator launch/receive system similar to the one shown in FIG. 13 but this one also incorporates a circular polarizer (isolator) in accordance with yet another embodiment of the present invention.

To reduce or eliminate these reflections, one may add some form of optical isolator 1802 to the single fiber collimator launch/receive system 106b as shown in FIG. 17. The optical isolator 1802 may be formed by placing a linear polarizer 1804 on top of the fiber lens 1402, and on top of the linear polarizer 1804 a quarter wave plate 1806 with its optical axis at 45° to the polarizer transmission axis may be placed.

Figure 18:
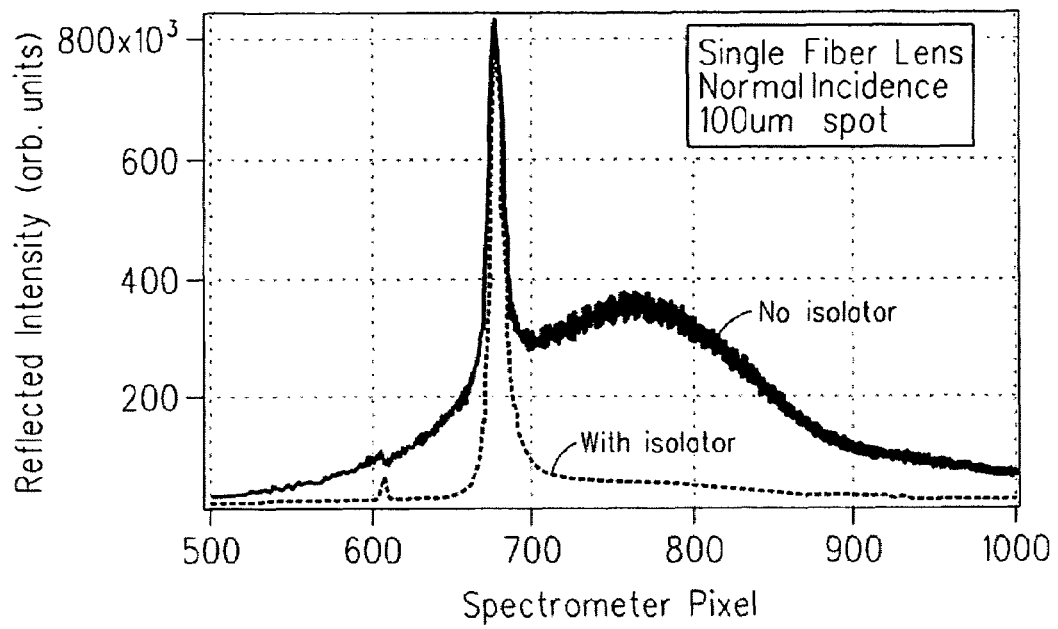
FIG. 18 is a graph illustrating a reflected spectrum from a RWG sensor interrogated at normal incidence with and without the circular polarizer (isolator) in the single fiber launch/receive system.

The spectral output of such an enhanced single fiber launch/receive system 106b' is shown in FIG. 18. These two additional components 1804 and 1806 create the circular polarizer 1802 which rejects Fresnel reflections but allows resonant reflections to pass. The circular polarizer 1802 causes all light 124/126 passing through it to become circularly polarized, and if the polarization is unchanged upon reflection as is the case with a Fresnel reflection, this same circular polarization will be blocked when traveling back through the circular polarizer 1802.

A detailed discussion is provided next to describe the optical model that was used to confirm some of the capabilities and features of the single fiber launch/receive system 106b. In particular, the following discussion describes the modeling and measurement of the resonance at normal incidence when using the single fiber launch/receive system 106b.

1. Description of the Model at High Incidence Angle

A possible method for modeling finite size input beams 124 includes decomposing the incident beam 124 into a sum of infinite plane waves and then applying to each of those waves a reflection coefficient that was calculated by using the RCWA modeling method. These equations are as follows:

First, decompose the incident wave:

$$Ei(r) := \int FFPi(k) \cdot \exp(i \cdot k \cdot r) dk \qquad (4.1)$$

$$FFPi(k) := TF(Ei(x))$$

$$k := 2 \cdot \pi \cdot \frac{\sin(\theta)}{\lambda}$$

where:
Index i stands for 'incident'.
FFP stands for far field pattern.
TF stands for Fourier transform.

Then, to calculate the energy distribution of the beam 126 reflected by the grating 114, we apply the incident Far Field Pattern as a function of a reflection coefficient which is a function of the wavelength $\lambda$ and the projection of the incident k vector along the grating vector as follows in equation 4.2:

$$FFPr(k, \lambda) := FFPi(k, \lambda) \cdot R(kx, \lambda) + r \cdot FFPi(k, \lambda)$$

$$R(kx, \lambda) := \frac{k01 \cdot k10}{\alpha + i \cdot \Delta k}$$

$$\Delta k := \frac{2 \cdot \pi}{\lambda} \cdot \left(-neff + \frac{\lambda}{\Lambda}\right) + k_x \quad \text{(Forward mode)}$$

$$\Delta k := \frac{2 \cdot \pi}{\lambda} \cdot \left(-neff + \frac{\lambda}{\Lambda}\right) - k_x \quad \text{(Backward mode)}$$

After using the above equations to calculate the electric field of the reflected wave, the total amount of power collected, or effective total reflectivity of the resonance from the sensor was determined by calculating the cross integral product of this electric field with the electric field output of the SM fiber 110.

Figure 19:
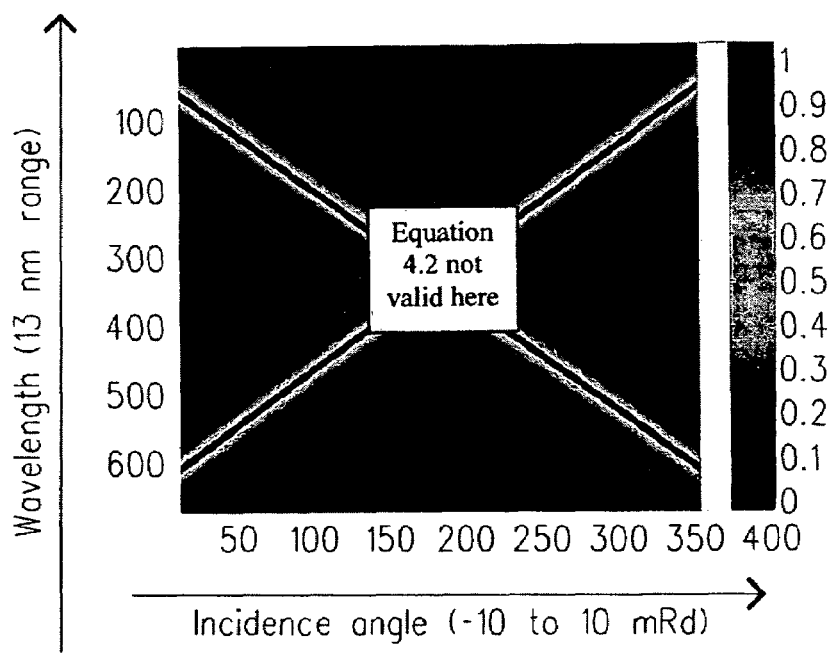
FIGS. 19-28 are various graphs and charts indicating the results of experiments that were conducted to confirm some of the capabilities and features of the single fiber launch/receive system.

This model can be applied to calculate, for instance, the resonance shape as a function of the diameter of the input and output beams 124 and 126. To help better explain what is happening, the plot in FIG. 19 is used where the absolute value of the reflectivity is shown as a function of the incidence angle (X-axis) and of the wavelength (Y axis). In this plot, the first approximation of the mode dispersion was neglected and the leakage coefficient was assumed to be the same for backward and forward propagating modes. This plot shows, for instance, that when one fixes an angle (on a vertical line) then one gets two symmetric resonances corresponding to the backward and forward propagating modes. However, when one gets closer to the normal incidence, the backward and forward propagating modes are not independent anymore and start interfering so that equation no. 4.2 is no longer valid.

Figure 20:
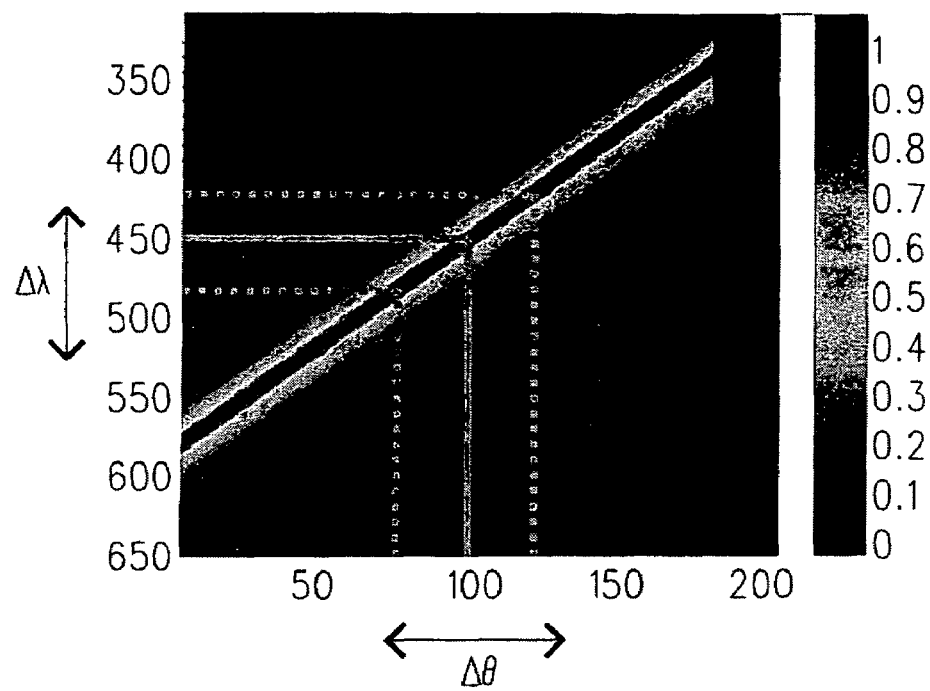

This plot can also be used to explain why the peak power of the resonance decreases and its width increases when using smaller beam diameters. To explain this, we use one arm of the previous graph which is shown in FIG. 20. First, consider an incident Gaussian beam which has a diameter that corresponds to a given angular spread $\Delta\theta$ in the Fourier space. Then, the smaller the beam size, the larger the angular spread. When increasing the angular spread, one can see on the graph that this also increases the wavelength spread because, for each incidence angle there is a range of resonant wavelength. Thus, decreasing the beam size increases the resonance width.

Additionally, consider only the central wavelength. If one draws a horizontal line, only the incident angles that are close to the maximum of the resonance angle are reflected, the other angles are lost. So, when increasing the angular range, the percentage of light that is reflected decreases. Thus: decreasing the beam size decreases the peak power of the resonance.

Figure 21:
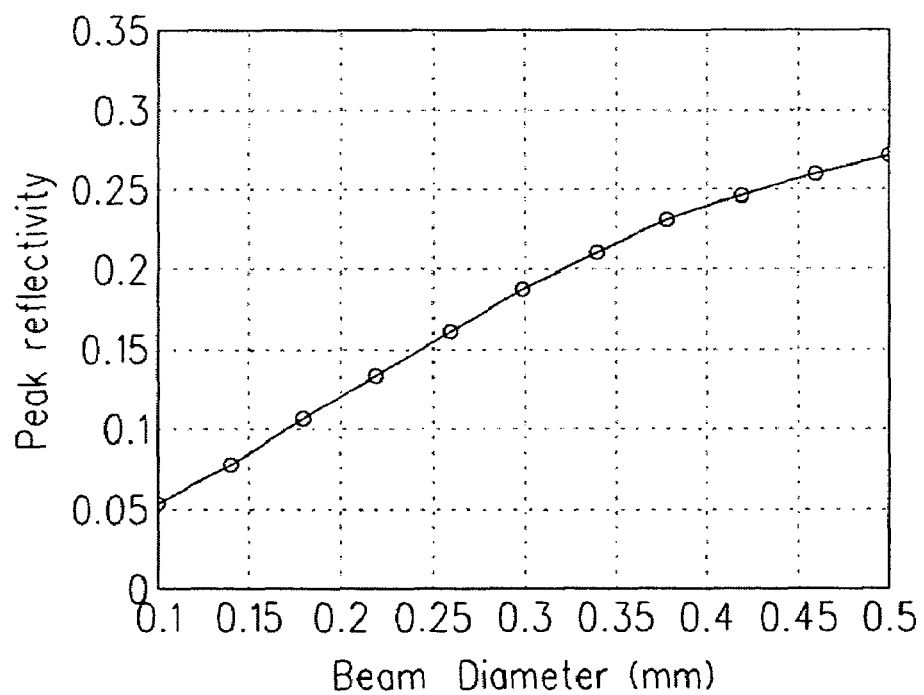
Figure 22:
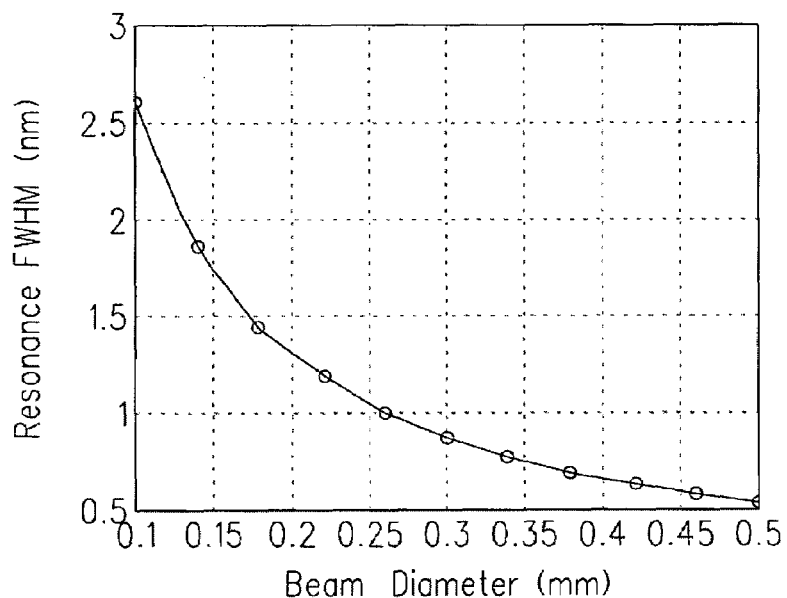

To illustrate these two basic rules, the following charts in FIGS. 21 and 22 show the evolution of the resonance peak power and resonance width as a function of the diameter of the incident beam 124.

If we now calculate the coupling efficiency that we get in a SM/SM configuration, based on the previous equations, we get the following result:

$$\text{Coupling} := \exp\left[-2 \cdot \left(\frac{\delta k}{k0}\right)^2\right] \cdot \int \left(\frac{k_{10} \cdot k_{01}}{\alpha + i \cdot \Delta k} + k21\right) \cdot \exp\left[-2 \cdot \left[\frac{(k - k0i)}{k0}\right]^2\right] dk$$

Coupling = f (δk) * g (λ)
Where δk is proportional to the angular misalignment of the sensor This last equation shows that, when the sensor is angularly misaligned, the only thing that happens is that the amplitude of the resonance decreases but neither the shape or the position of the resonance are affected.

2. Description of the Model at Normal Incidence 2.1 Result of the Rigourous Coupled Wave Analysis (RCWA) Model Because of interference effects between the backward and forward propagating modes near normal incidence, equation no. 4.2 that describes the reflectivity versus the incident k vector and the wavelength is no longer valid, and one must use the RCWA method to calculate the 2-D reflectivity function.

The picture in FIG. 14 shows the reflectivity as a function of the wavelength (vertical axis) and the incident angle (horizontal axis) calculated with the RCWA method. As can be seen, each of the backward (lower curve) and forward (upper curve) resonance start being curved when they come closer to normal incidence and both curves do not cross each other at the center. As can also be seen, the forward propagating mode disappears at the proximity of the normal incidence.

2.2 Experimental Evidence

Figure 23:
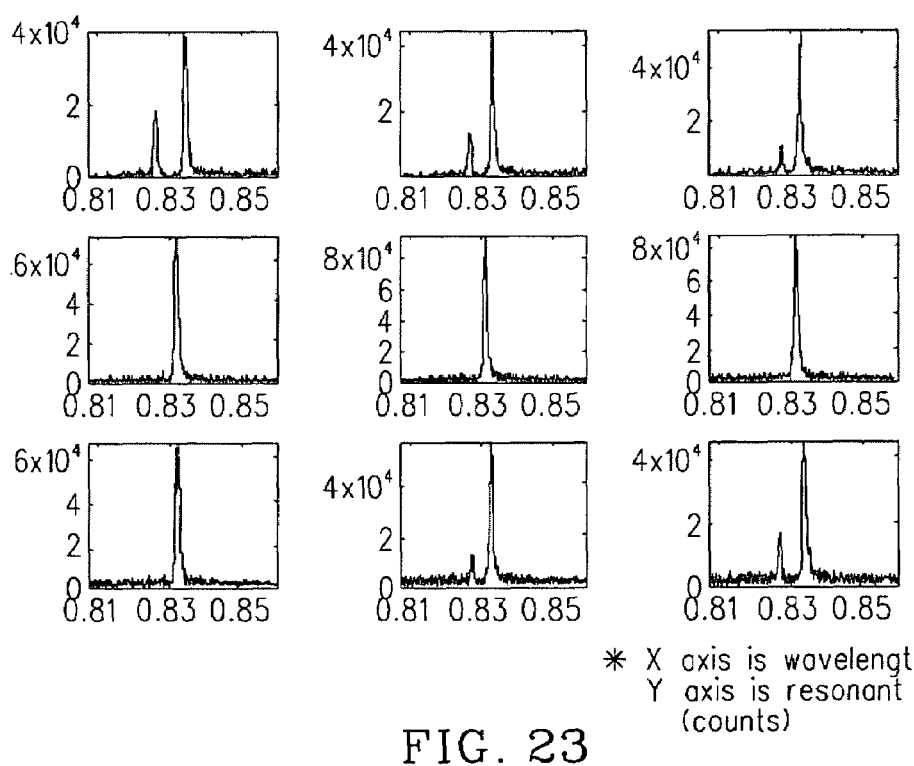
Figure 24:
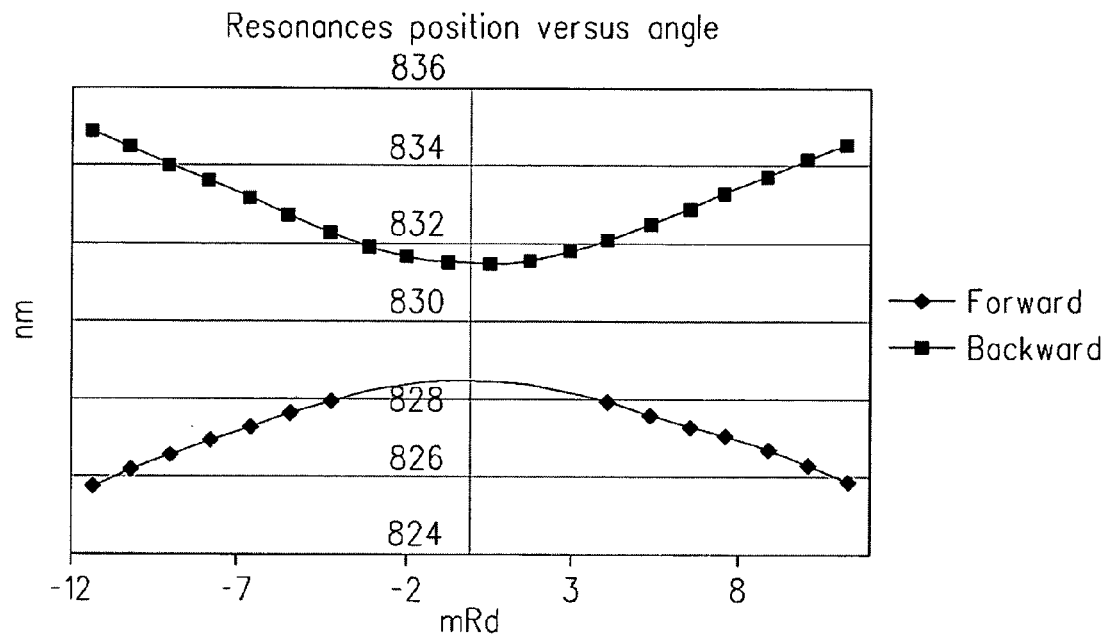
Figure 25:
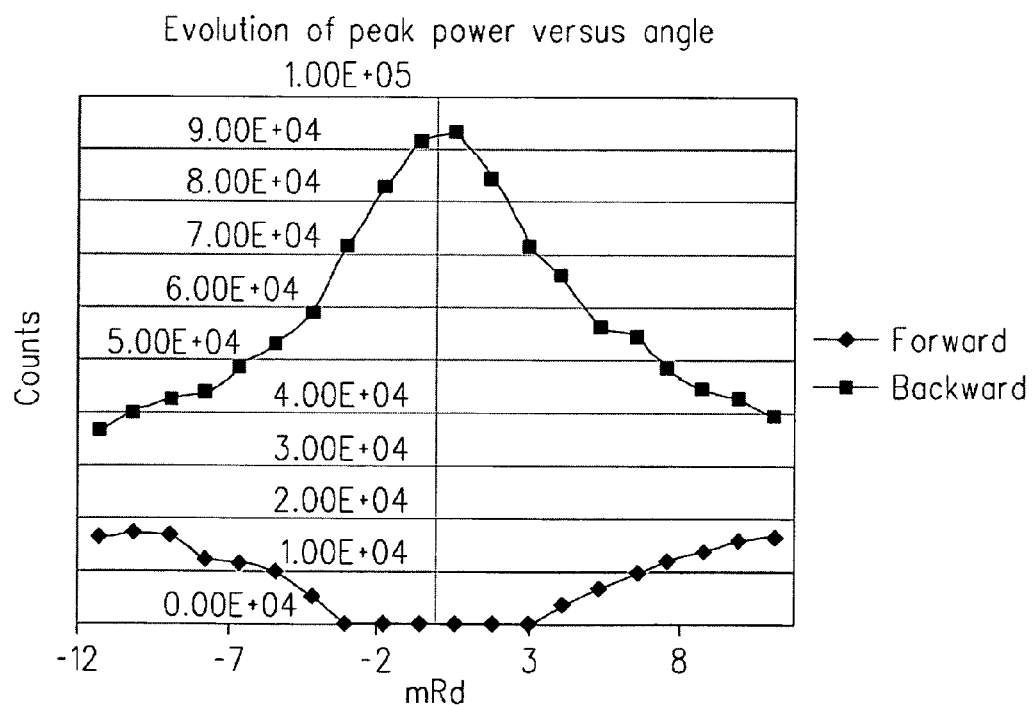

To experimentally validate the reflectivity curve, we used a multimode (MM) fiber launch/single mode (SM) receive system at near normal incidence. This allowed one to vary the sensor angle over a wide range while still collecting a substantial fraction of the reflected resonant light. FIG. 23 are plots that show the evolution of the resonance as a function of the tilt of the plate for an angle from −11 mRd to +11 mRd. As can be seen, when one comes close to the normal incidence, the peak power of the forward resonance (peak on the left) decreases but remains constantly separated from the backward resonance by a finite amount (peak on the right). This result is in agreement with the prediction of the RCWA model. Next, we utilized the data of FIG. 23 to determine their position and peak power of the respective resonant peaks as shown in FIGS. 24 and 25. It should be appreciated that FIGS. 23 and 24 are results of resonant wavelength and amplitude and resonant power distilled from the data shown in FIG. 22.

3. Advantage of Normal Incidence

Figure 15:
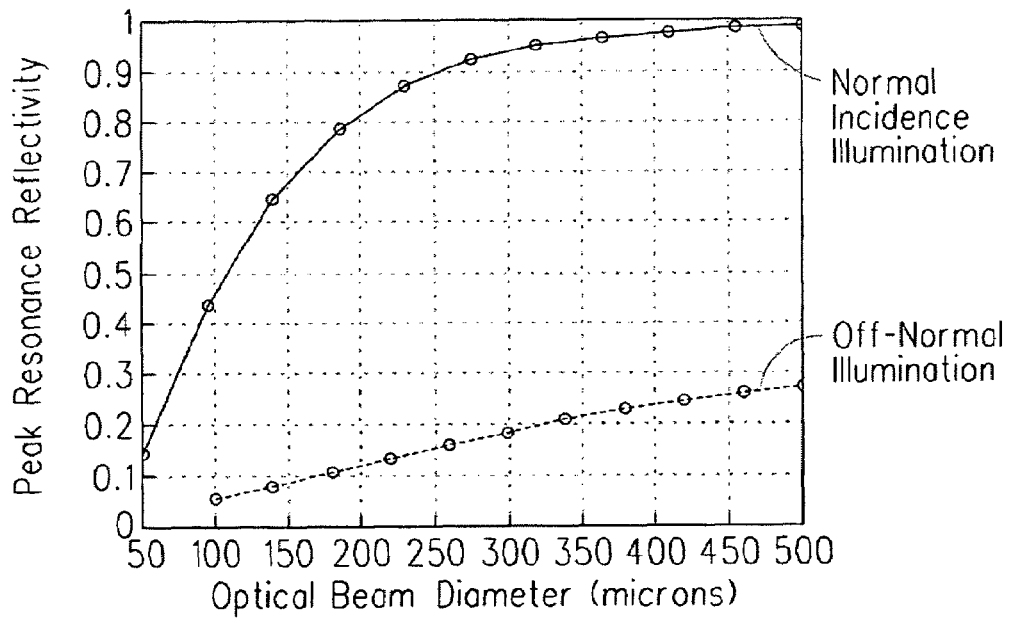
FIG. 15 is a graph illustrating a peak resonance reflectivity as a function of optical beam diameter for normal incidence illumination and off-normal incidence illumination using a single fiber launch/receive system.
Figure 16:
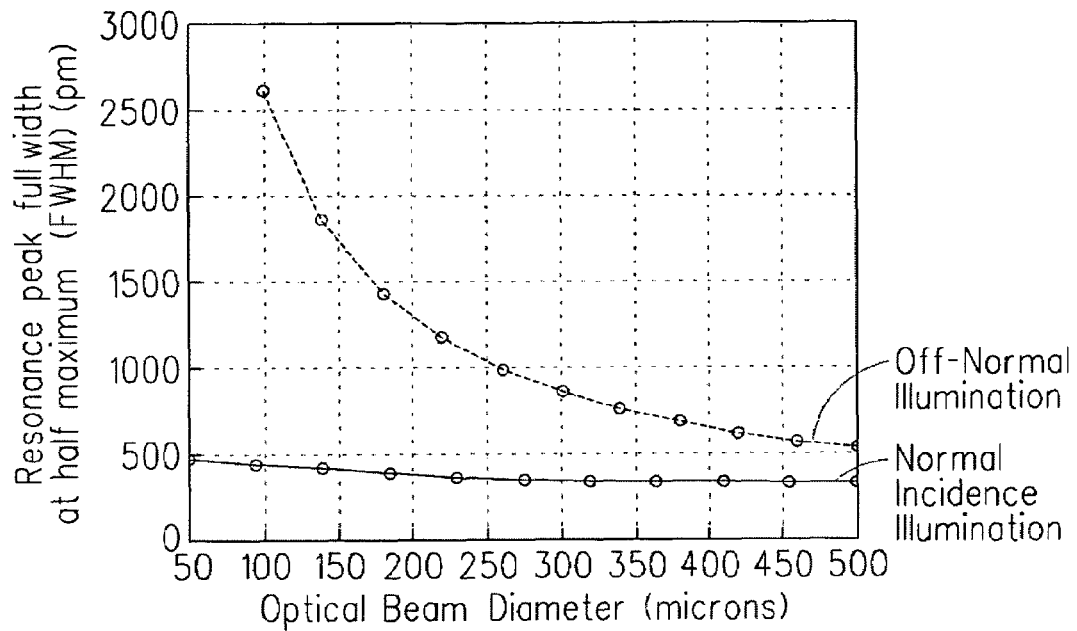
FIG. 16 is a graph illustrating a resonant peak full width half maximum (FWHM) as a function of beam diameter for normal incidence illumination and off-normal incidence illumination using a single fiber launch/receive system.
Figure 26:
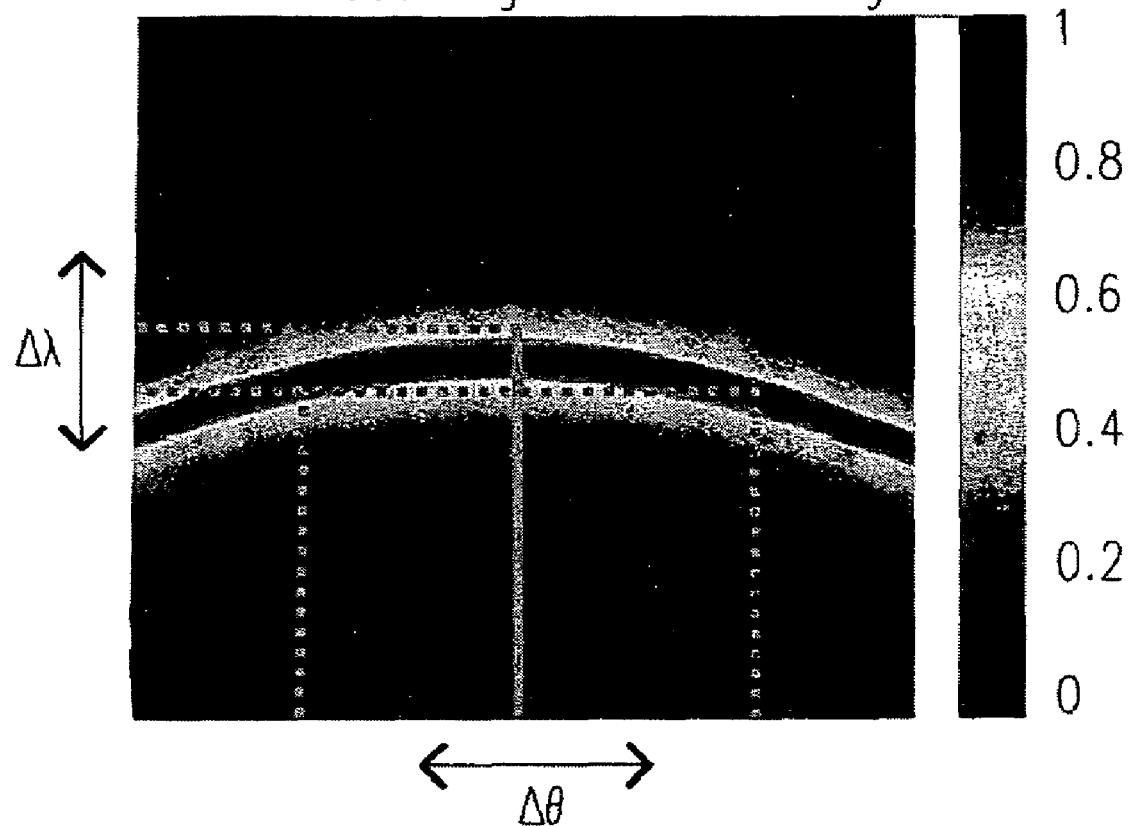

One advantage of using normal incidence is to enable smaller incident beam diameters which make the interrogation system 100 less sensitive to angular misalignments. Referring back to the discussion of the peak resonance shape versus the beam diameter presented in section 1, if one considers that the reflectivity is a parabolic curve, then it can be seen that the resonance enlargement due to an increase of the angular spread is much lower than in the case of the linear function shown in FIG. 26. On the other hand, if one utilizes a wavelength which intersects the curve near the top of the hyperbole (near normal incidence), then one observes that a wider range of angles are reflected efficiently for this wavelength than for wavelengths that intersect the curve far away from normal incidence. Therefore, for interrogation near normal incidence, the amplitude of the reflected resonance will be least affected by an increase of the input beam angular spread. FIGS. 15 and 16 show this evolution of the peak reflectivity and peak FWHM versus the beam diameter calculated respectively at normal incidence and at high incidence angle. As can be seen, there is an advantage in using the normal incidence configuration in terms of diffraction efficiency and width of the resonance, especially when decreasing the beam diameter.

4. Experimental Results at Normal Incidence

TABLE #1 summarizes the results obtained from a given RWG sensor when inserting different lenses 1402 into the optical path to reduce the size of the beam 124.

TABLE #1

|  | No lens High incidence | No lens Normal incidence | Focal 50 mm Normal incidence | Focal 25 mm Normal incidence | units |
|---|---|---|---|---|---|
| Beam diameter | 0.5 | 0.5 | 0.1 | 0.052 | mm |
| Measured Peak | 9.1 | 28.4 | 23 | 12 | % reflectivity |
| Expected Peak | 32 | 100 | 43 | 14 | % reflectivity |

TABLE #1-continued

|  | No lens High incidence | No lens Normal incidence | Focal 50 mm Normal incidence | Focal 25 mm Normal incidence | units |
|---|---|---|---|---|---|
| Measured FWHM | 700 | 750 | 810 | 910 | pm |
| Expected FWHM(*) | 700 | 525 | 650 | 720 | pm |
| Angular tolerance(**) | 1 | 1 | 3.4 | 7.1 | mRd |

(*)Calculated taking into account the spectrometer response.
(**)Diameter of the angular tolerance corresponding to a 50% drop in power.

Although a non-negligible difference can be seen between the expected values and the measured values which are probably due to grating imperfections, the general conclusion is that one can reduce the beam diameter by a factor of 10 without sacrificing much reflection efficiency or increasing the resonance width appreciably.

5. Considerations when Utilizing a Small Beam at Normal Incidence

By using a focused beam at normal incidence, one may think that the design is similar to a MM configuration in that the input beam is not well collimated. For instance, at first glance one may expect to get the same huge sensitivity of 500 pm/mRd. However, by focusing the beam on the RWG sensor, we image the Gaussian beam and we are then in an optimum SM configuration. So, as explained above, the optical models show that the SM launch/receive design is almost entirely insensitive to angular misalignment (either off normal incidence or at normal incidence).

Figure 27:
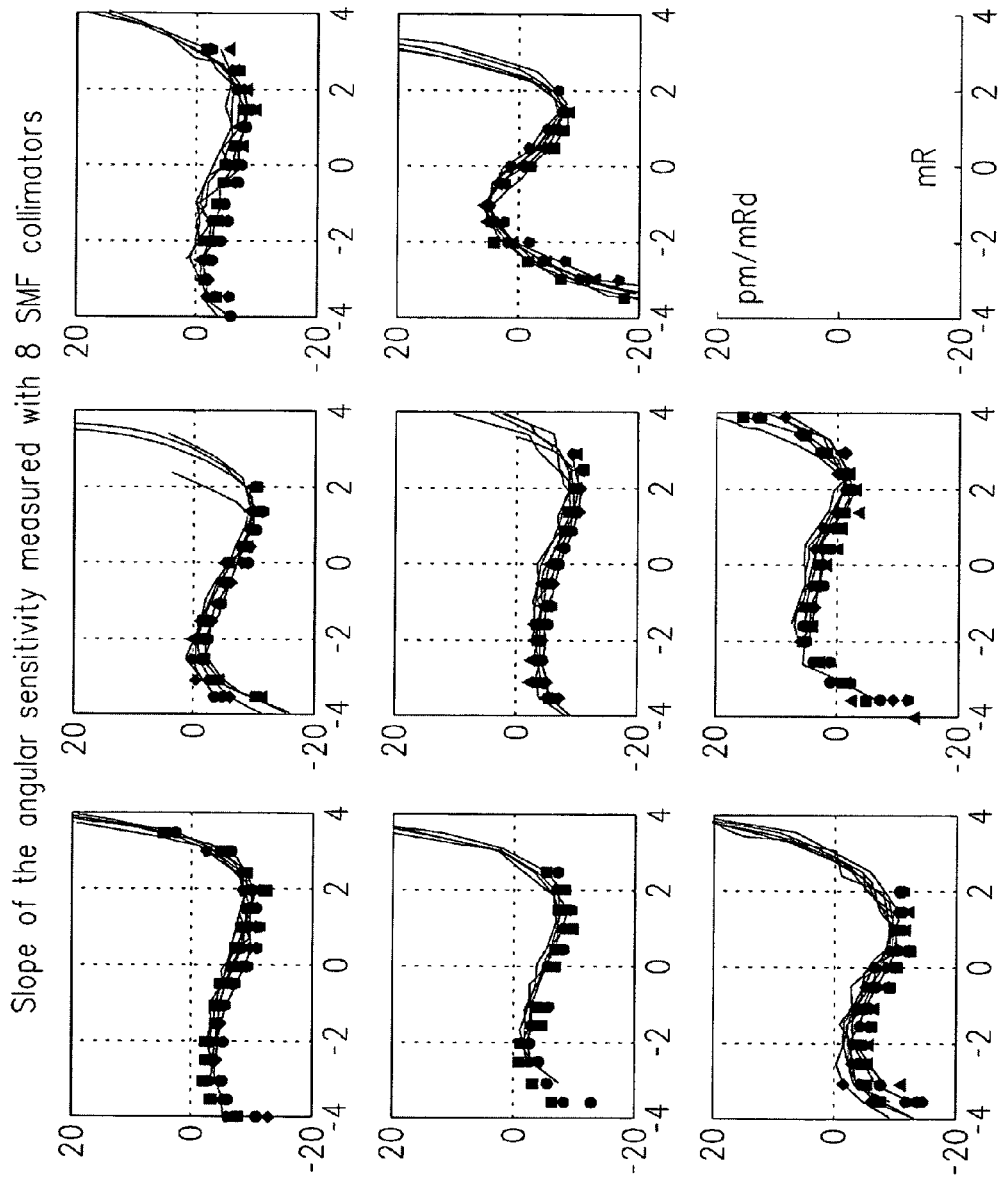

FIG. 27 shows several graphs where the angular sensitivity of the resonance position was measured at normal incidence with a beam diameter of 100 microns versus the tilt of the plate. As can be seen, the sensitivity is approximately 10 pm/mRd which is orders of magnitude below the sensitivity of the MM configuration.

Figure 28:
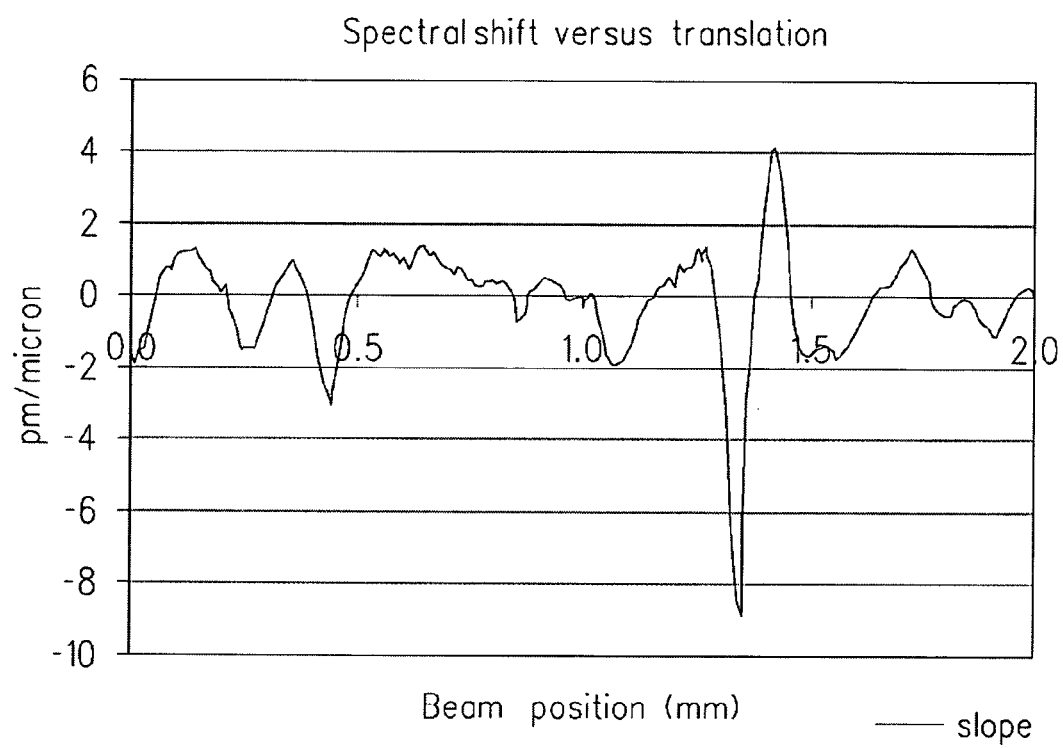

A potential problem which may be caused by reducing the beam diameter is that the measurement becomes more sensitive to local defects in the sensor. FIG. 28 is a graph that shows the change in resonance wavelength as a function of the lateral motion of the sensor. As can be seen, there are spectral shifts of up to 2 pm/micron everywhere and there are even some local defects that where generated with up to 8 pm/microns. Likewise, another concern is that if there is a large non-homogeneity in the amount of biochemical binding across the sensor, then the small beam may make the system more sensitive to these spatial variations, increasing the amount variation (or coefficient of variance, CV) in the binding signal. However, judicious practices in the fabrication of the sensor itself, in the surface chemistry applied to the sensor, and in the fluid handling used to introduce the biochemicals to the sensor, may be used to mitigate these problems. Additionally, scanning of the optical beam and spatial integration of the data over the sensor surface may be used to reduce the spatial sensitivities of small spot interrogation. For example, refer to U.S. patent application Ser. No. 11/027,547 entitled "Spatially Scanned Optical Reader System and Method for Using Same". The contents of this document are incorporated by reference herein.

From the foregoing, it can be readily appreciated by those skilled in the art that what has been described herein is a SM optical fiber launch/receive system 106 which uses one or more SM optical fibers 110 to interrogate a biosensor 102 and does not use any MM optical fibers to interrogate the biosensor 102. The use of the SM optical fiber launch/receive system 106 effectively reduces angular sensitivity, reduces unwanted system reflections, improves overall angular tolerance, and improves resonant peak reflectivity and resonant peak width. Also, described herein are two specific embodiments of the SM optical fiber launch/receive system 106 including: (1) a dual fiber collimator launch/receive system 106a; and (2) a single fiber launch/receive system 106b that interrogates the biosensor 102 at a normal incidence.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A system, comprising:
   a light source;
   a light detector; and
   a dual fiber collimator launch/receive system which includes:
      a first single mode optical fiber to output a sensor input beam to a biosensor; and
      a second single mode optical fiber to receive a sensor output beam from the biosensor,
   wherein said biosensor is a resonant waveguide grating sensor.

2. A system, comprising:
   a light source;
   a light detector; and
   a dual fiber collimator launch/receive system which includes:
      a first single mode optical fiber to output a sensor input beam to a biosensor; and
      a second single mode optical fiber to receive a sensor output beam from the biosensor, wherein said first and second single mode optical fibers are physically separated from a lens located a predetermined distance away from the biosensor which enables the rejection of Fresnel reflections and parasitic reflections which are created while interrogating the biosensor, 3. A system, comprising:
   a light source;
   a light detector; and
   a dual fiber collimator launch/receive system which includes:
      a first single mode optical fiber to output a sensor input beam to a biosensor; and a second single mode optical fiber to receive a sensor output beam from the biosensor, wherein said first and second single mode optical fibers are physically separated from a lens located a predetermined distance away from the biosensor that effectively creates an input grating and an output grating out of a single grating within the biosensor while interrogating the biosensor.

4. A system, comprising:
a light source;
a light detector; and
a dual fiber collimator launch/receive system which includes:
  a first single mode optical fiber to output a sensor input beam to a biosensor; and
  a second single mode optical fiber to receive a sensor output beam from the biosensor, wherein said first and second single mode optical fibers are physically separated from a lens located an adjustable distance away from the biosensor which enables one to measure a loss coefficient alpha α of the biosensor.

5. A system, comprising:
a light source;
a light detector; and
a dual fiber collimator launch/receive system which includes:
  a first single mode optical fiber to output a sensor input beam to a biosensor; and
  a second single mode optical fiber to receive a sensor output beam from the biosensor, wherein the use of the first and second single mode optical fibers within said dual fiber collimator launch/receive system eliminates undesirable spatial modes which would be present if multimode optical fibers were used within said dual fiber collimator launch/receive system.

6. A system, comprising:
a light source;
a light detector; and
a dual fiber collimator launch/receive system which includes:
  a first single mode optical fiber to output a sensor input beam to a biosensor; and
  a second single mode optical fiber to receive a sensor output beam from the biosensor, wherein the use of the first and second single mode optical fibers within said dual fiber collimator launch/receive system causes said dual fiber collimator launch/receive system to have less sensitivity, in terms of wavelength variation, to angular deviations of the biosensor than if multimode optical fibers were used within said dual fiber collimator launch/receive system.

7. A system, comprising:
a light source;
a light detector; and
a dual fiber collimator launch/receive system which includes:
  a first single mode optical fiber to output a sensor input beam to a biosensor; and
  a second single mode optical fiber to receive a sensor output beam from the biosensor, wherein the use of the of the first and second single mode optical fibers within said dual fiber collimator launch/receive system causes a resonant wavelength associated with the biosensor to be more stable than if multimode optical fibers were used within said dual fiber collimator launch/receive system.

8. A method for interrogating a biosensor, said method comprising the steps of:
  using a dual fiber collimator launch/receive system which does not have multimode optical fibers incorporated therein to interrogate the biosensor, wherein said dual fiber collimator launch/receive system includes:
    the first single mode optical fiber;
    the second single mode optical fiber; and
    a lens, wherein said first single mode optical fiber is interfaced with a light source, wherein said first and second single mode optical fibers are physically separated from said lens and said lens is physically separated from said biosensor, wherein said first single mode optical fiber emits a light beam generated by said light source such that the emitted light beam is passed through said lens before interfacing with the biosensor, wherein said biosensor reflects the light beam such that the reflected light beam passes through said lens and said second single mode optical fiber and is received by a light detector, and wherein said biosensor is located within a microplate; and
  moving said microplate and said biosensor relative to said dual fiber collimator launch/receive system which enables the emitted light beam to be scanned across different areas on said biosensor while interrogating said biosensor.

9. The method of claim 8, wherein the use of the first and second single mode optical fibers within said dual fiber collimator launch/receive system eliminates undesirable spatial modes which would be present if multimode optical fibers were used within said dual fiber collimator launch/receive system.

10. The method of claim 8, wherein the use of the first and second single mode optical fibers within said dual fiber collimator launch/receive system causes said dual fiber collimator launch/receive system to have less sensitivity, in terms of wavelength variation, to angular deviations of the biosensor than if multimode optical fibers were used within said dual fiber collimator launch/receive system.

11. The method of claim 8, wherein the use of the of the first and second single mode optical fibers within said dual fiber collimator launch/receive system causes a resonant wavelength associated with the biosensor to be more stable than if multimode optical fibers were used within said dual fiber collimator launch/receive system.

12. The method of claim 8, wherein said biosensor is a resonant waveguide grating sensor.

* * * * *